United States Patent
Fan et al.

(10) Patent No.: US 6,727,501 B1
(45) Date of Patent: Apr. 27, 2004

(54) METHOD FOR DETECTING OVER-ETCH DEFECTS

(75) Inventors: Yong-Hui Fan, Cupertino, CA (US); Jay Rathert, San Jose, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 10/052,852

(22) Filed: Nov. 2, 2001

Related U.S. Application Data

(60) Provisional application No. 60/326,881, filed on Sep. 27, 2001.

(51) Int. Cl.[7] .................... G21K 7/00; G01R 31/26
(52) U.S. Cl. ................ 250/307; 250/311; 324/765; 324/751; 257/48
(58) Field of Search ................. 250/307, 311; 324/765, 751; 257/48

(56) References Cited

U.S. PATENT DOCUMENTS

| | | | | |
|---|---|---|---|---|
| 5,430,292 A | * | 7/1995 | Honjo et al. | 250/310 |
| 5,923,430 A | * | 7/1999 | Worster et al. | 356/394 |
| 6,410,353 B1 | * | 6/2002 | Tsai | 438/14 |
| 6,495,856 B2 | * | 12/2002 | Kikuchi | 257/48 |
| 6,504,393 B1 | * | 1/2003 | Lo et al. | 324/765 |

* cited by examiner

*Primary Examiner*—John R. Lee
*Assistant Examiner*—Paul M. Gurzo

(57) ABSTRACT

An over-etched defect in a semiconductor wafer is detected by applying an electrical field to the contacts in a first area and comparing the intensity measured with the intensity from a reference area. In one embodiment, one of the contacts in each of the first and reference areas is a gate contact in an MOS device and a second contact is either a source or drain contact. The selected charging field forward biases the pn junctions between the source and drain regions and the well in which they are formed. As a result, defects caused by gate contacts shorted to one of the source and drain contacts are visible using voltage contrast imaging techniques.

14 Claims, 5 Drawing Sheets

METHOD FOR DETECTING OVER-ETCH DEFECTS

CROSS-REFERENCE TO RELATED APPLICATION

This application takes priority under U.S.C. 119(e) of United States Provisional Application No.: 60/326,881 filed Sep. 27, 2001 entitled, "METHOD FOR DETECTING OVER-ETCH DEFECTS" Yong-Hui Fan and Jay Rathert, which is incorporated by reference in its entirety for all purposes.

BACKGROUND OF THE INVENTION

The present invention relates generally to detection of defects in semiconductor device processing. More specifically, the present invention relates to methods of detecting over-etch defects in devices having pn junctions.

As semiconductor devices shrink in size, new challenges present themselves. The shrinking in device sizes is often accompanied by an increase in the number of contacts and especially self-aligning contacts. The rising number of self-aligning contacts is making overall contact formation more challenging. Detecting defects such as over-etch in self-aligning contact formation is likewise increasingly challenging.

Current automated optical imaging and light-scattering inspection technologies have limited success detecting defects within high aspect ratio structures such as self-aligning contacts which are becoming more prevalent as device sizes adjacent to gates in the formation of metal oxide semiconductor field effect transistors (MOSFET or MOS).

When a contact is over-etched, the spacer adjacent to a gate is etched into and may easily cause a short or cause leakage between the source and/or the drain contact and the polysilicon or polysilicide gate. In many cases, the defect shorting the gate and the source or drain regions will escape detection by conventional inspection techniques.

However, such defects may be inspected after fabrication of the device is complete and electrically tested. For example, the source or drain and gate pads may be electrically probed for shorts. Unfortunately, waste of time and materials may be expended if detection of defects must await final device assembly. Destructive techniques are also available off-line after specific process steps but render the tested device unusable. That is, the wafer is removed from the clean room to undergo electrical probing. Once removed, the wafer cannot be reinserted into the process flow.

Therefore, what is needed is a non-destructive in-line method for detecting over-etch defects in MOS devices at an early stage of the fabrication process using inspection equipment that is available during the process flow, such as a scanning electronic beam microscope (SEM).

SUMMARY OF THE INVENTION

To achieve the foregoing, the present invention provides apparatus and methods for detecting over-etch defects associated with contacts in a semiconductor device. An over-etched defect is detected by applying an electrical field to the contacts in a candidate area and comparing the intensity measured with the intensity from a reference area. In one embodiment, one of the contacts in each of the candidate and reference areas is a gate contact in an MOS device and a second contact is either a source or drain contact. The selected electrical charging field forward biases the pn junctions between the source and drain regions and the well in which they are formed. As a result, defects caused by gate contacts shorted to one of the source and drain contacts are visible using voltage contrast imaging techniques. In other words, a defective contact has a different imaged appearance during a voltage contrast inspection than a non-defective reference contact. In one embodiment, if a minority of imaged contacts have a different appearance than a majority of imaged contacts, the minority are determined to be defective.

In one aspect, the present invention provides a method of detecting an over-etched defect. An electrical field is applied above a wafer having a candidate area and a reference area. Each of the candidate area and the reference area has a portion with a first contact connected to a pn junction and a second contact separated by a spacer from the first contact. The electrical field is selected to forward bias the pn junction. An intensity difference of detected electrons between contacts in the candidate area and the reference area is determined. In a further aspect, it is determined that a defect exists when the intensity difference exceeds a predetermined threshold.

In another aspect, the inspected portion of the wafer is a PMOS device and an extracting electrical field is applied. The first contact is either a source or drain contact and the second contact is a gate contact.

In yet another aspect of the invention, the inspected portion of the wafer is an NMOS device and a retarding electrical field is applied. The first contact is either a source or drain contact and the second contact is a gate contact.

These and other features and advantages of the present invention are described below with reference to the drawings.

DETAILED DESCRIPTION OF SPECIFIC EMBODIMENTS

Reference will now be made in detail to specific embodiments of the invention. Examples of these embodiments are illustrated in the accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
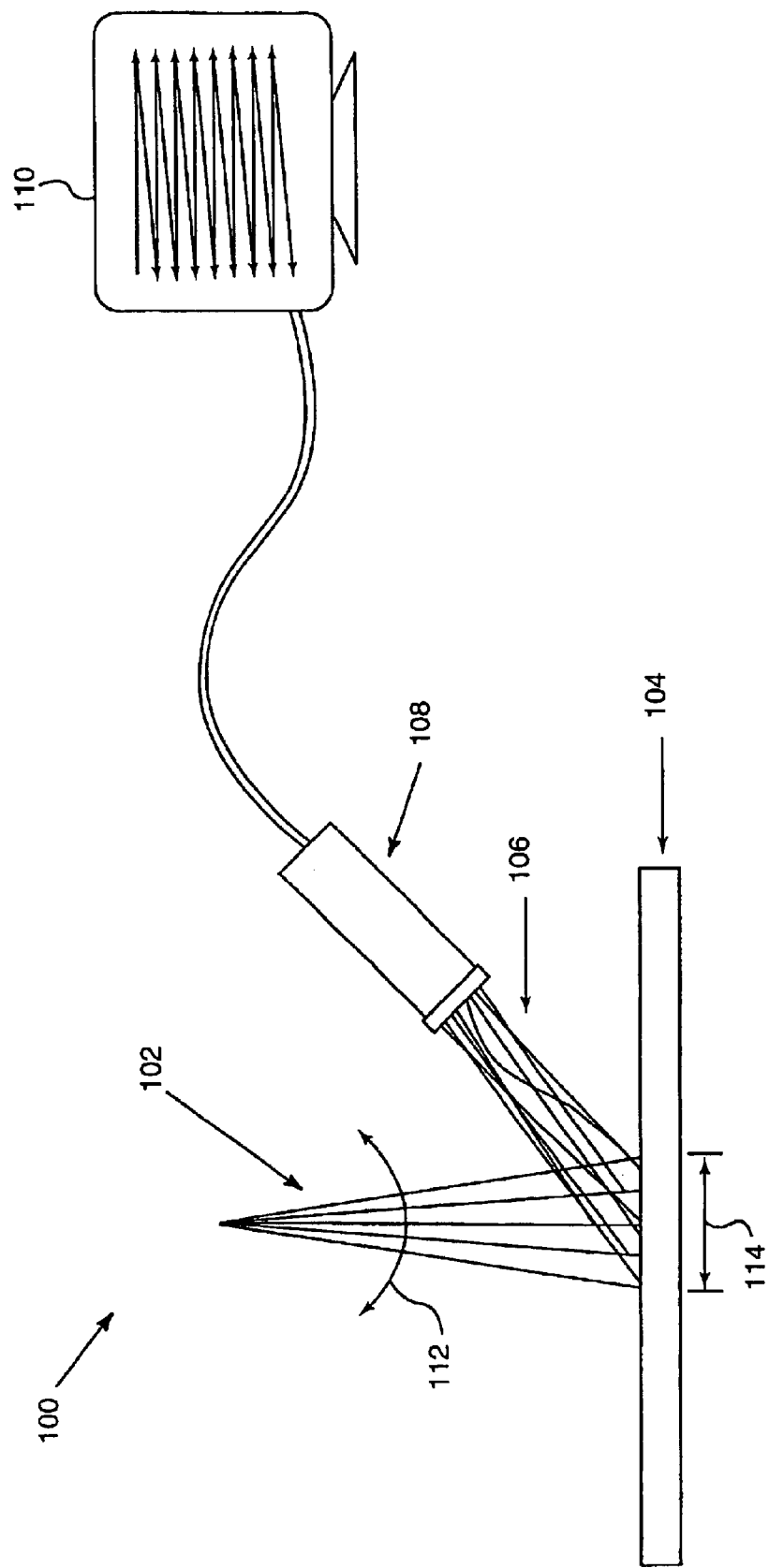
FIG. 1 is a diagrammatic representation of a scanning electron microscopy configuration that may be configured to implement the techniques of the present invention.

Over-etch defects create unique challenges in inspection. In the present invention, over-etch defects involving contacts connected to pn junctions may be detected using scanning electron microscopes and voltage contrast techniques through the select application of a controlling charge. FIG. 1 is a diagrammatic representation of a scanning electron microscopy configuration 100 that may be configured to implement the techniques of the present invention. As shown, a beam of electrons 102 is scanned over a sample 104 (e.g., a semiconductor wafer). Multiple raster scans 112 are typically performed over a small area 114 of the sample 104. The beam of electrons 102 either interact with the sample and cause an emission of secondary electrons 106 or bounce off the sample as backscattered electrons 106. The secondary electrons and/or backscattered electrons 106 are then detected by a detector 108 that is coupled with a computer system 110. The computer system 110 generates an image that is stored and/or displayed on the computer system 110.

A certain amount of secondary electrons may be required to provide a satisfactory image. This quantity of secondary electrons helps bring out the contrast features of the sample. The SEM system may include one or more electrodes configured to control charge on the sample. The electrode(s) are placed proximal to the sample and charged to a predetermined voltage. In general terms, the predetermined voltage results in the generation of an electric field that functions to control charge on the surface of the sample.

The predetermined voltage is selected to repel some of the electrons emitted from the sample back towards the sample such that charge accumulated on the surface of the sample is controlled. For example, a portion of the secondary electrons emitted from the sample may be repelled back to the sample surface to cancel positive charge or build up negative charge on the sample surface. This is an example of a retarding field. As a result, the surface may be negatively charged. A negative surface charge increases the energy of escaping electrons whereas a positive charge decreases it. The predetermined voltage may also be selected to form an extracting field. An extracting field attracts electrons from the surface of the wafer thus leaving the surface positively charged.

The contrast in the image caused by localized voltage differences on the sample surface is referred to as a voltage contrast effect. Generally, electrons emitted from a candidate area detected by the detector are used to generate an image that is compared to a corresponding image of a reference area. In one embodiment of the present invention, the image of the contacts in the candidate area is compared with the image obtained from reference areas on the wafer.

Voltage contrast techniques make it possible to detect over-etch defects created during the fabrication of metal-oxide semiconductor field-effect transistors (MOSFET or MOS). MOS transistors are popular. A common form, (PMOS) is fabricated in the n-well on a p-type substrate or on an n-type substrate. Two heavily doped p-type regions are created in the substrate. Contacts are made to the source region and the drain region. A gate contact is typically placed between the source and drain regions above an oxide layer grown on the substrate. The substrate forms pn junctions with the source and drain regions. These are kept reverse biased during normal operation, thus cutting off current flow across the junctions.

Figure 2:
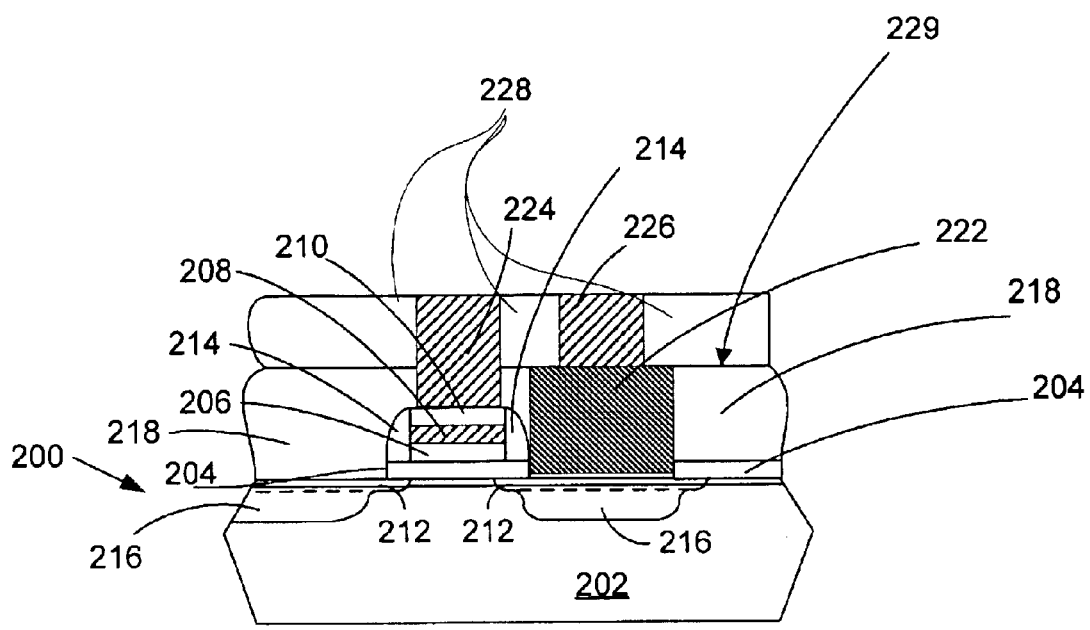
FIG. 2 is a cross-sectional diagram of an MOS device formed by conventional processing.

An example of an MOS device, such as used within memory devices, is illustrated in FIG. 2. The device 200 is formed on a semiconductor substrate 202, typically composed of monocrystalline silicon. The device 200 is formed according to a series of fabrication steps well known to those of skill in the art. First, isolation regions (not shown) are formed on the substrate 202. Then a gate oxide layer 204 is formed on the surface of the substrate 202.

Next, a layer of polysilicon 206 is formed on the gate oxide layer, typically by using a chemical vapor deposition (CVD) process well known to those with skill in the art. This polysilicon deposition step is followed by deposition of additional layers of material, also typically using CVD. Silicide layer 208 is the first additional layer and may, for example, be composed of tungsten silicide ($WSi_x$), which is referred to as a "polycide" when deposited in this manner. The second layer, dielectric 210, is a dielectric material that is resistant to a subsequent etching procedure. Typical examples of this material include silicon oxynitride (SiON) or silicon nitride ($Si_3N_4$).

This three-layer stack is then patterned and etched to form distinct gates. The etch chemistry should have good selectivity to oxide so that the gate oxide material (204) exposed by the etch on either side of the gates prevents penetration into the substrate.

Once the gate has been formed, an implant is performed to produce a shallow diffusion region 212 at the surface of the substrate 202 to form source and drain regions. Then, sidewall spacers 214 are formed in a conventional manner by deposition of an oxide (TEOS), oxynitride, or nitride layer followed by an anisotropic etch. Deep implants 216 are then formed according to conventional procedures. Following formation of the sidewall spacers 214 and diffusion regions 212/216, an interlayer dielectric 218 may be formed. A second interlayer dielectric or oxide layer 228 may also be formed.

Many process variations may be used to fabricate an equivalent structure as shown in FIG. 2. These processes will produce contacts by patterning and etching one or more dielectric layers then filling those contact holes (e.g. vias) with a conductive material to form a gate contact (224) and an interconnect (226) to the source/drain (222) contact. For example tungsten may be deposited to form the conductive contacts. At this point, a chemical mechanical polishing (CMP) step typically is performed to planarize the surface of the partially completed device.

Over-etching defects may occur during anisotropic etching in the formation of the sidewall spacers 214 or during etching of the oxide (dielectric) layers (218, 228), thus creating the potential for electrical leakage or shorts from the gate contact 224 to the source/drain contacts 222,226.

In normal situations, during inspection, the gate contacts (e.g., 224) are floating, i.e. they are at a voltage level independent of ground. In some cases where the source or drain contacts are grounded, the defective gate contacts can be isolated using electron beam inspection. The defective gates (i.e., those shorted to the contacts for the source or drain regions) will in this case also be grounded and will exhibit different charging characteristics than a normal floating gate contact during an electron beam inspection. These voltage contrast effects may thus be detected. However, the source or drain contacts are not always grounded. The present invention detects over-etch defects by using voltage contrast techniques and forward biasing the pn junctions at the source and drain regions through the selective application of extracting and retarding fields.

More specifically, the present invention takes advantage of the fact that normally gate contacts are floating to discern between "good" gates and shorted gates (i.e. those shorted due to over-etching). The gates float under normal conditions because of their placement over the isolating gate oxide 204 layer.

Figure 3:
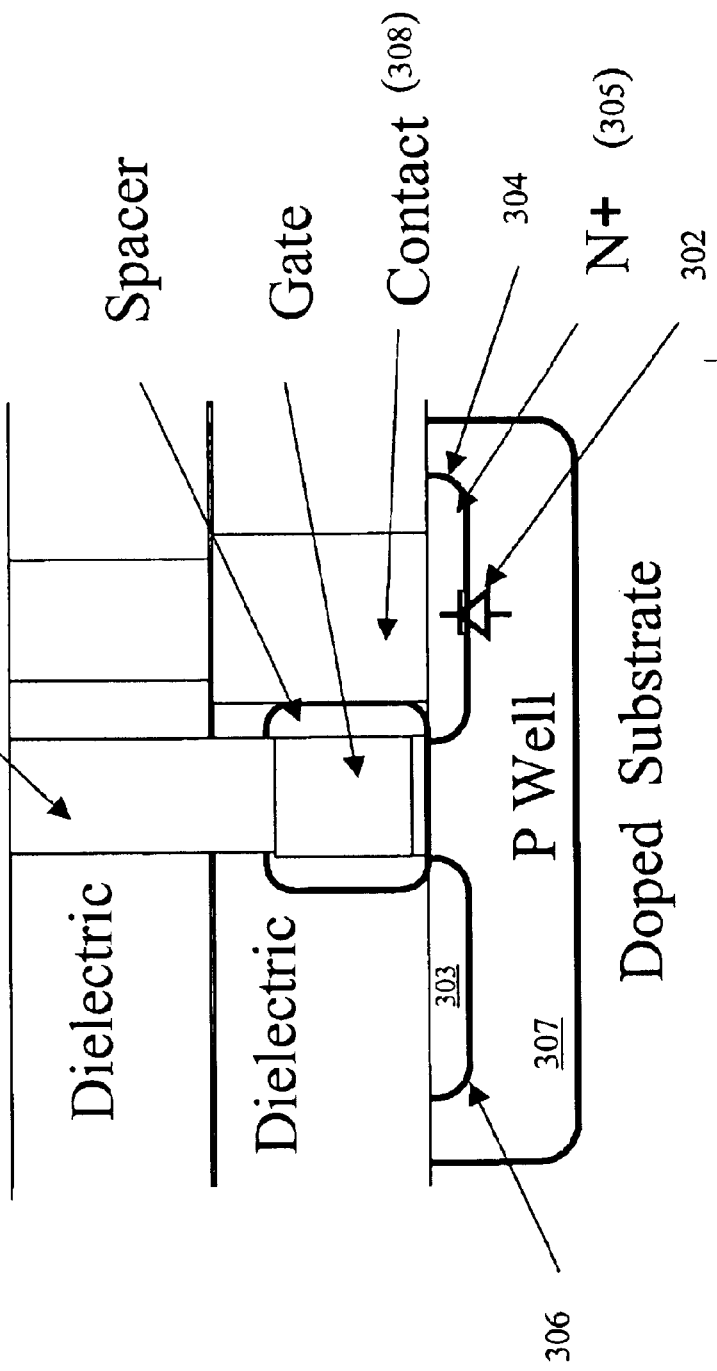
FIG. 3 is a diagrammatic representation of an NMOS device in accordance with one embodiment of the present invention.

In an NMOS device, the n+ regions 303, 305 form a pn junction with a surrounding p-well 307. This is shown by the diode symbol 302 in FIG. 3. Application of a retarding field by the electron beam inspection equipment (e.g., SEM) will produce a negative surface charge on the semiconductor device. The retarding field is adjusted to a point where a forward bias is reached and pn junctions 304, 306 are turned on. This charge will result in a forward bias voltage applied to the pn junctions 304,306. These forward biased pn junctions will permit current to flow across the junctions thereby allowing source/drain contact 308 to be electrically connected to the substrate which is commonly grounded during voltage contrast inspection.

Over-etch defects may be detected in these situations with voltage contrast techniques. An image taken of a reference sample will show a normal reference image intensity for a normal gate contact (310), i.e. one that is at a floating voltage level. A shorted gate contact (310), however, will be grounded and produce an image intensity for this candidate area comparable to the intensity of the grounded source and drain regions in the image. In this instance, the retarding field enables the electronic beam inspection system, utilizing the voltage contrast effect, to detect the defects. In contrast, defective (i.e. shorted) gates would be indistinguishable from normal gates where an extraction field is applied to the NMOS device. This occurs because the pn junctions are cut off and thus the source and drain regions are at a floating voltage level, as are the defective gates and the normal gates.

Figure 4:
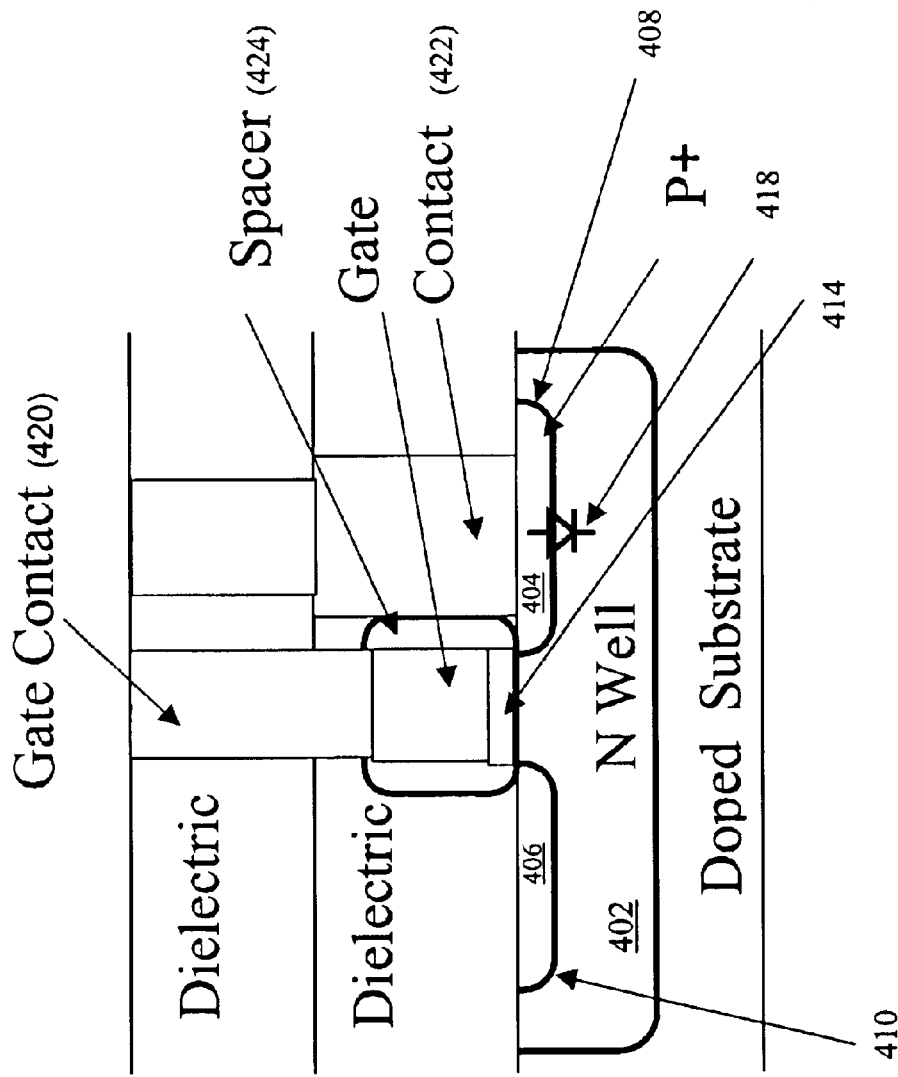
FIG. 4 is a diagrammatic representation of a PMOS device in accordance with one embodiment of the present invention.

Similar techniques may be applied to detect over-etch defects in PMOS devices. As shown in FIG. 4, a PMOS device will have an n-well 402 implanted into the substrate. The p+ regions 404, 406 are created for the source and drain. The gate contact 420 is normally floating because of the presence of gate oxide 414. Over-etching will cause the gate contact 420 to become shorted with the source/drain contact 422 through the spacer 424. In the PMOS device, the p+ regions 404, 406 create pn junctions 408,410 with the surrounding n-well 402. Diode symbol 418 indicates that the normal flow of current from the p+ region 404 to the n-well 402. In this situation, an extracting field must be applied by the electron beam inspection equipment to create a positive surface charge. Such a surface charge will forward-bias (turn on) the pn junctions 408, 410 permitting current flow from the p+ regions 404, 406 to the n-well 402. Thus, the gate contacts 420 become grounded with source/drain contact 422. This allows the over-etched spacers or insulation dielectric layers and shorted gate contacts to be detected using the electron beam inspection and voltage contrast effects, as described above.

In contrast, a retarding field would apply a negative surface charge and would turn off the pn junctions 408, 410, thus rendering the defective gates to be indistinguishable by voltage contrast techniques from normal gates. In sum, voltage contrast techniques, therefore, would not be able to detect over-etch defects unless a retarding field was applied to an NMOS device or an extracting field was applied to a PMOS device.

The etching defect created during the anisotropic etching may be suitably inspected, in one embodiment, within several process steps of the creation of the defect using the voltage contrast techniques of the present invention. For example, after application of an extracting or retarding field the voltage contrast inspection may take place following the deposition of a conductor fill metal such as tungsten into the contact holes etched into oxide layer 228 (as shown in FIG. 2) and a subsequent chemical mechanical polishing (CMP) step. Prior to this point over-etch defects in the sidewall spacers or other insulators may not be filled with conductive material. Thus, there may not be an electrically conductive path between the polysilicon gate and the source/drain contacts until the deposition of the contact fill material such as tungsten. The inspection described may be performed at a lower level, i.e. level 229 as shown in FIG. 2, if gate contact 224 and source/drain contact 222 are composed of the same material.

Figure 5:
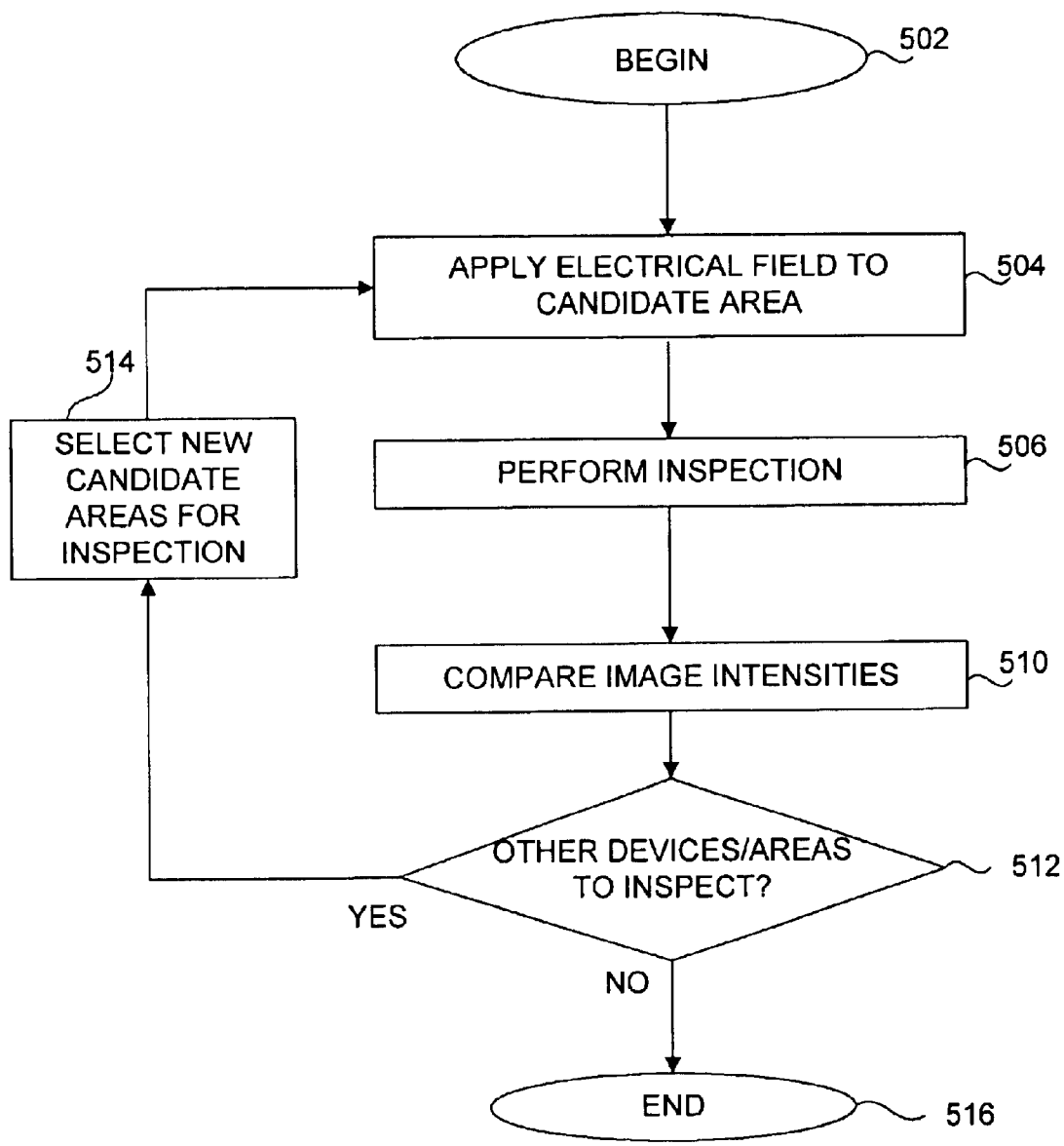
FIG. 5 is a flowchart illustrating a method of inspecting an MOS device in accordance with one embodiment of the present invention.

FIG. 5 is a flowchart illustrating a method of inspecting an MOS device in accordance with one embodiment of the present invention. The method ideally would occur after the Contact CMP level had been completed, i.e. the contact holes had been filled with a conductive material and a flat surface had been provided on the partially formed semiconductor using CMP methods. Initially, a selected electrical charging field would be applied to the candidate area by the scanning electron microscope system (504). In one embodiment, the candidate area is one die on a wafer and the reference area is a second die on a wafer. The invention is not limited to such embodiments. The reference areas may comprise a different portion of the same die or may correspond to an image from another wafer, for example, in other embodiments. As noted above, an extracting field would be applied to a PMOS device and a retarding field would be applied to an NMOS device. The electrical field selected would forward bias the pn junction located between a contact being tested and ground (the substrate) in the semiconductor subject to testing.

An inspection using an SEM system and voltage contrast techniques would then typically provide an image corresponding to the quantities of electrons detected from the inspected areas of the device (506). An inspection of a reference area using the same equipment and electrical charging voltage would follow as part of the inspection step (506). In order to determine defects, the image from the product candidate area would be compared to the reference area (510). In one embodiment, the candidate area is compared with reference images from two adjacent dies. Determining if a defect exists is based on the premise that any difference in image intensities between contacts in the candidate areas and contacts in the reference areas represents a defect. For example, if a minority of the contacts have a different imaged appearance during the voltage contrast inspection than a majority of contacts, then the minority of contacts are determined to be defective. If other types of devices, areas, or dies need testing (512), steps 504–512 may be repeated. For example, the initial electrical charging field applied might be effective to detect over-etch defects in PMOS devices. A different electrical field (e.g. retarding field) would then be applied to test the NMOS devices or to complete testing of a complementary metal oxide semiconductor (CMOS) device.

Although the foregoing invention has been described in some detail for purposes of clarity of understanding, it will be apparent that certain changes and modifications may be practiced within the scope of the appended claims. It should be noted that there are many alternative ways of implementing both the method and apparatus of the present invention. Accordingly, the present embodiments are to be considered as illustrative and not restrictive, and the invention is not to be limited to the details given herein, but may be modified within the scope and equivalents of the appended claims.

What is claimed is:

1. A method of detecting an over-etched defect in the formation of a semiconductor device using a scanning electron microscope comprising:

applying an electrical field to at least one semiconductor device, each of the at least one semicondcutor devices comprising an exposed gate electrode and at least one of source and drain contacts, the source and drain contacts connecting respectively to source and drain diffusions, each of the diffusions forming a pn junction with one of a well or substrate region, wherein the electrical field is selected to forward bias the pn junction; and detecting electrons emitted from the exposed gate electrode surface to determine the presence of a defect between the gate and one of the source and drain contacts.

2. The method as recited in claim 1, wherein the at least one semiconductor device comprises at least two devices and further comprising determining an intensity difference between the detected electrons emitted from the gate electrode surfaces of the first and the second of the at least two devices.

3. The method as recited in claim 2 further comprising:
determining that a defect exists when the intensity difference exceeds a predetermined threshold.

4. The method as recited in claim 2 wherein each of the at least two devices is an MOS device.

5. The method as recited in claim 4 wherein the MOS device is a PMOS device and the electrical field applied is an extracting field.

6. The method as recited in claim 5 wherein the pn junction is at least one of an interface between a source region and the N-well of the PMOS device and the interface between the drain region and the N-well of the PMOS device.

7. The method as recited in claim 4 wherein the MOS device is an NMOS device and the electrical field applied is a retarding field.

8. The method as recited in claim 7 wherein the pn junction is at least one of an interface between a source region and the P-well of the NMOS device and the interface between the drain region and the P-well of the NMOS device.

9. The method as recited in claim 4 wherein the applying an electrical field and the determining the intensity difference occurs after contact holes connected to the gate and at least one of the source and drain regions have been filled with a conducting material.

10. The method as recited in claim 4 wherein the applying an electrical field and the determining the intensity difference occurs after conducting material has been deposited in the contact holes connected to the gate and at least one of the source and drain regions and after chemical mechanical polishing of the deposited conducting materials.

11. The method as recited in claim 4 wherein the applying an electrical field occurs after the semiconductor process steps of filling contact holes with a conductive material and before further fabrication steps are performed on the semiconductor.

12. The method as recited in claim 4 wherein the applying an electrical field occurs after the semiconductor process steps of depositing a conductive material in the contact holes and performing a CMP step on the filled contacts and before further fabrication steps are performed on the semiconductor.

13. The method as recited in claim 1 wherein a scanning electron microscope system applies the electrical field to the wafer.

14. The method as recited in claim 1 wherein an electrode applies the electrical field to the wafer.

* * * * *